United States Patent [19]
Koulbanis et al.

[11] Patent Number: 5,997,885
[45] Date of Patent: *Dec. 7, 1999

[54] COSMETIC AND/OR DERMATOLOGICAL COMPOSITION CONTAINING THERMAL SPRING WATER OR MINERAL WATER AND AN ACTIVE AGENT, IN ORDER TO COMBAT ACNE OR AGING

[75] Inventors: Constantin Koulbanis, Le Kremlin-Bicetre; Jean-Pierre Laugier, Antony; Francoise Gagnebien-Cabanne, Chatillon; Sabine Deprez, Thiais, all of France

[73] Assignee: L'Oreal, Paris, France

[ * ] Notice: This patent is subject to a terminal disclaimer.

[21] Appl. No.: 08/926,967

[22] Filed: Sep. 10, 1997

Related U.S. Application Data

[63] Continuation of application No. 08/505,484, Jul. 21, 1995, Pat. No. 5,690,946.

[30] Foreign Application Priority Data

Jul. 22, 1994 [FR] France .................... 94 09119

[51] Int. Cl.$^6$ .............. A61K 6/00; A61K 7/00; A61K 31/74
[52] U.S. Cl. ........................ 424/401; 424/78.03
[58] Field of Search ..................... 424/401, 450; 514/828, 859, 937, 861, 944, 844

[56] References Cited

U.S. PATENT DOCUMENTS

| | | | |
|---|---|---|---|
| 4,318,907 | 3/1982 | Kligman et al. | 424/230 |
| 4,767,750 | 8/1988 | Jacquet et al. | 514/159 |
| 5,262,407 | 11/1993 | Leveque et al. | 514/159 |
| 5,376,379 | 12/1994 | Fabre et al. | 424/450 |
| 5,520,918 | 5/1996 | Smith | 424/401 |
| 5,690,946 | 11/1997 | Koulbanis et al. | 424/401 |

OTHER PUBLICATIONS

Database, WPI, Week 9506, Derwent Publications, Ltd., London, GB; AN 95–041193, Abstract of JP–A–06 321 789.
Database WPI, Week 9509, Derwent Publications, Ltd., London, GB; AN 95–065701, Abstract of SU–A–1 833 733.
Database WPI, Week 8026, Derwent Publications Ltd., London, GB; AN 80–45798C, Abstract of JP–A–55 065 298.

*Primary Examiner*—Thurman K. Page
*Assistant Examiner*—Sharon Howard
*Attorney, Agent, or Firm*—Oblon, Spivak, McClelland, Maier & Neustadt, P.C.

[57] ABSTRACT

Cosmetic compositions containing water having a mineralization of at least 400 mg/l and an active agent having an irritant side effect exhibit a reduced irritant effect; the water is especially a thermal spring water and/or mineral water and the active agent is especially a keratolytic agent of the salicylic acid derivative type.

19 Claims, No Drawings

COSMETIC AND/OR DERMATOLOGICAL COMPOSITION CONTAINING THERMAL SPRING WATER OR MINERAL WATER AND AN ACTIVE AGENT, IN ORDER TO COMBAT ACNE OR AGING

This is a Continuation of application Serial No. 08/505,484 filed on Jul. 21, 1995, allowed on May 27, 1997.

BACKGROUND OF THE INVENTION

1. Field of the Invention

The present invention relates to cosmetic and/or dermatological compositions based on thermal spring water and/or mineral water for mildly treating the skin of the human body and/or face, including the scalp, while at the same time hydrating it. The present invention also relates to the use of such compositions for the cosmetic treatment of acne, wrinkles and/or fine lines on the skin.

2. Discussion of the Background

The active agents commonly used for the treatment of acne, wrinkles, and/or fine lines on the skin include keratolytic agents chosen from α- and β-hydroxy acids and derivatives thereof, retinoids and derivatives thereof and especially retinoic acid (all-trans and 13-cis) and retinol, and benzoyl peroxide.

Among the β-hydroxy acids are, in particular, salicylic acid and derivatives thereof. Salicylic acid is known for the treatment of acne (see EP-A-281,812) and wrinkles (see WO-A 93/10755), and some of the derivatives of this acid are known for the treatment of ageing of the skin and especially for delaying and/or attenuating the appearance of wrinkles and fine lines (see EP-A-378,936).

Retinoic acid is also known for preventing the appearance of wrinkles and/or fine lines on the skin.

Moreover, these keratolytic agents are known to modify the complexion of the skin, which appears rosier, to fade out pigmented marks present at the surface, to eliminate squama and to improve the elasticity of the skin.

Unfortunately, once applied to the skin, these keratolytic agents cause itching, stinging and tightness which may lead to considerable discomfort, owing to the attack on the keratin in the skin caused by such agents.

Furthermore, the use of these products by consumers with sensitive skin is often prevented.

Mineral water present in the form of liposomes in cosmetic compositions is already known for the purpose of hydrating the surface and deep layers of the skin (see FR-A-2,608,426).

Moreover, FR-2,668,063 teaches the use of liposomes of thermal spring water which are stabilized in a DNA gel for the preparation of cosmetic compositions. Such a form of use of thermal spring water allows, according to this document, its targeted penetration into the dermis and epidermis of the skin.

Unfortunately, these liposomal compositions based on thermal spring water or on mineral water do not allow the treatment of wrinkles, fine lines and/or acne present on the skin of the human body and/or face or on the scalp.

Thus, there remains a need for cosmetic and/or dermatological compositions based on thermal spring water and/or mineral water which allow the skin to be rejuvenated and which allow acne spots to be removed, while at the same time avoiding the drawbacks mentioned above and in particular while promoting the hydration of the skin at the surface and deep down.

SUMMARY OF THE INVENTION

Accordingly, it is one object of the present invention is to provide novel cosmetic compositions for the treatment of acne, wrinkles, and/or fine lines on the skin.

It is another object of the present invention to provide novel cosmetic compositions for the treatment of acne, wrinkles, and/or fine lines on the skin which exhibit a reduced tendency to cause skin irritation.

It is another object of the present invention to provide a method of treating acne, wrinkles, and/or fine lines on the skin by applying such a composition to the skin.

These and other objects, which will become apparent during the following detailed description, have been achieved by the inventors' discovery that the keratolytic agents mentioned above act in particular by a mechanism of inflammation of the skin which, although mild, is sufficient to bring about this rejuvenated and healthy-looking appearance after application to the skin for a few months.

Thus, the inventors have discovered that using a thermal spring water or mineral water having a mineralization of at least 400 mg/l in a cosmetic and/or dermatological composition containing one or more keratolytic agents conserves inflammatory properties of these keratolytic agents while at the same time allowing the skin to be hydrated.

Thus, the present invention provides the use of a water having a mineralization of at least 400 mg/l in a cosmetic and/or dermatological composition containing at least one active agent having an irritant side effect, in order to remove this irritant effect. The water having a mineralization of at least 400 mg/l is especially a thermal spring water and/or mineral water.

The present invention also provides cosmetic and/or dermatological compositions comprising at least one active agent having an irritant side effect, in a cosmetically and/or dermatologically acceptable medium, and comprising a calming agent chosen from thermal spring waters and/or mineral waters having a mineralization of at least 700 mg/l.

DETAILED DESCRIPTION OF THE PREFERRED EMBODIMENT

In the present invention, the term "mineralization" refers to the sum of the concentrations of anions and cations present in the thermal spring water or mineral water. The fact that a water of high mineralization is used makes it possible, precisely, to compensate for the irritant effect of the cosmetic and/or dermatological active agents such as the keratolytic agents.

The present invention may either use a thermal spring water or a mineral water. In general, a mineral water is suitable for consumption, which is not always the case of a thermal spring water. Each of these waters contains, inter alia, solubilized minerals and trace elements. These waters are known to be employed for specific treatment purposes depending on the particular trace elements and minerals which they contain, such as the hydration and desensitization of the skin or the treatment of certain dermatoses. Thus, depending on the type of water used, it is possible, in addition to calming the irritant side effect of certain active agents, to treat the skin specifically.

Indeed, the more a water is mineralized, the harder it is to be incorporated into compositions owing to the ready formation of precipitates during the preparation of these compositions.

The thermal spring water and/or mineral water used according to the invention may have a mineralization of at least 700 mg/l, preferably 700–1,000 mg/l, and, in particular, a total concentration of carbonates and bicarbonates of at least 150 mg/l and preferably of at least 360 mg/l, more preferably 360–700 mg/l, and especially of sodium carbonate and bicarbonate of greater than 2 mg/l, preferably 2–10 mg/l. The concentration of silicon oxide in the water used in the composition according to the invention may preferably be at least 6 mg/l and more preferably at least 9 mg/l, even more preferably 9–70 mg/l.

The thermal spring water or the mineral water used according to the invention may be chosen from eau de Vittel, eaux du bassin de Vichy, eau d'Uriage, eau de la Roche Posay, eau de la Bourboule, eau d'Enghien-les-bains, eau de Saint-Gervais-les-bains, eau de Néris-les-bains, eau d'Allevard-les-bains, eau de Digne, eau des Maiziéres, eau de Neyrac-les-bains, eau de Lons le Saunier, Eaux Bonnes, eau de Rochefort, eau de Saint Christau, eau des Fumades and eau de Tercis-les-bains.

Among these waters, those which have a mineralization of less than 700 mg/l but greater than 400 mg/l are eau de la Roche Posay, Eaux Bonnes and eau de Saint Christau.

Among these waters, those which have a total concentration of carbonates or bicarbonates of greater than 360 mg/l are eau de Vittel, eau de la Bourboulee, eau des Fumades, eau d'Enghien-les-bains, eau de la Roche Posay, eau du bassin de Vichy and eau d'Uriage.

Among these waters, those which have a concentration of carbonates or bicarbonates of between 150 mg/l and 360 mg/l are eau de Digne, eau de Maiziéres, eau de Rochefort and eau de Saint-Gervais-les-bains.

Among these waters, those which contain at least 2 mg/l of sodium carbonate or bicarbonate are eau de la Roche Posay, eau de Vittel, eaux du bassin de Vichy, and eau d'Uriage.

The waters containing at least 9 mg/l of silicon oxide are eau de la Roche Posay, eau de Vittel, eaux du bassin de Vichy and eau d'Uriage.

The agent with an irritant side effect is, in particular, a keratolytic agent but may also be an antifungal, antibacterial or anti-seborrhoeic agent.

The keratolytic agent used according to the invention may be chosen from α-hydroxy acids (glycolic acid, mandelic acid, lactic acid, tartaric acid and citric acid), β-hydroxy acids and derivatives thereof, retinoids (retinoic acid or retinol) and derivatives thereof, benzoyl peroxide and the salts of these various compounds.

The keratolytic agent is preferably a β-hydroxy acid, such as salicylic acid or one of the derivatives thereof, which is optionally salified. The keratolytic agent is preferably a salicylic acid derivative which is optionally salified. Salicylic acid derivatives which may in particular be mentioned are those described in FR-A-2,581,542 and EP-A-378,936, and particularly 5-n-octanoylsalicylic acid, 5-n-decanoylsalicylic acid, 5-n-dodecanoylsalicylic acid, 5-n-octylsalicylic acid, 5-n-heptyloxysalicylic acid, 4-n-heptyloxysalicylic acid, and the quaternary ammonium salts thereof such as the dimethylhydroxypropylammonium salts. It is also possible to use the salicylic acid derivatives described in EP-A-570,230.

The composition according to the invention preferably comprises eau du bassin de Vichy and 5-n-octanoylsalicylic acid.

The proportion of keratolytic agent in the composition according to the invention ranges, for example, from 0.1% to 5% by weight based on the total weight of the composition. This proportion preferably ranges from 0.1% to 2% by weight based on the total weight of the composition.

The thermal spring water or mineral water is preferably present in an amount greater than 0.1% by weight based on to the total weight of the composition and, for example, at least equal to 5% by weight, and better still ranging from 5% to 75%. The thermal spring water or mineral water may have distilled or demineralized water added to it in the composition.

Another advantage of the composition according to the present invention is to be able to use, in cosmetic and/or dermatological compositions, thermal spring waters or mineral waters having both high concentrations of carbonate and bicarbonate ions and a high concentration of positive ion, such as sodium and calcium, without the fear of the formation of a calcium precipitate, owing to the acidic nature of the keratolytic agent.

The composition according to the present invention may be in the form of a solution, an aqueous gel, an emulsion (oil-in-water or water-in-oil emulsion) or a dispersion of lipid vesicles and have the appearance of a lotion, a serum, a cream or a gel. It may additionally comprise at least one lipophilic or hydrophilic active agent other than the agent with an irritant side effect and chosen in particular from screening agents, ceramides, proteins and hydrolysates thereof, and hydrating agents.

The composition according to the invention may furthermore comprise at least one cosmetically and/or dermatologically acceptable additive chosen from surfactants (emulsifying agents and co-emulsifying agents), fats, preserving agents, fragrances, gelling agents, complexing agents and neutralizing agents.

The present invention also relates to the use of the composition defined above for the cosmetic treatment of acne, wrinkles and/or fine lines on the skin and to the use of this composition for the preparation of a dermatological ointment intended for the treatment of acne, wrinkles and/or fine lines. The present invention also relates to a process for the cosmetic treatment of acne, wrinkles and/or fine lines on the skin, consisting in applying the composition defined above to the skin.

Other features of the invention will become apparent in the course of the following descriptions of exemplary embodiments which are given for illustration of the invention and are not intended to be limiting thereof.

EXAMPLES

An example of a composition in accordance with the invention is given below. The amounts therein are given as a percentage by weight. The term "qs 100%" means that that ingredient is present in an amount such that the total amount of all ingredients equals 100% by weight.

Example: O/W emulsion intended for the treatment of facial skin

| Fatty phase: | |
|---|---|
| Apricot almond oil (oleic-linoleic acid triglycerides) | 14.5% |
| Liquid fraction of karite butter (palmitic-stearic-oleic-linoleic acid triglycerides) | 7.0% |
| Propyl para-hydroxybenzoate (preserving agent) | 0.1% |
| Fatty alcohol mixture (stearyl alcohol, | 1.0% |

-continued

| | |
|---|---|
| arachidylic alcohol and behenyl alcohol) | |
| Sorbitan monostearate (Span 60 from ICI) | 2.5% |
| Mixture of cetylstearyl 2-ethylhexanoate and isopropyl myristate (purcellin oil) | 2.0% |
| Aqueous phase: | |
| Preserving agents | 0.5% |
| Ethylenediaminetetraacetic acid.2H$_2$O disodium salt (complexing agents) | 0.05% |
| Neutralizing agent | 0.5% |
| Gelling agent | 0.7% |
| Glycerol | 5.0% |
| Oxyethylenated sorbitan monostearate (20 EO) (Tween 60 from ICI) (surfactant) | 2.5% |
| 5-n-octanoylsalicylic acid | 1 |
| Eaux du bassin de Vichy | 62.65% |
| Demineralized or ion-exchanged water | qs 100% |

The emulsion is in the form of a white cream intended for the treatment of wrinkles, due to ageing, and for the hydration of the skin.

Among the various mineral waters and/or thermal spring waters mentioned above, the Applicant has found, by means of comparative tests, that eau du bassin de Vichy had a greater power to calm the irritation caused by a keratolytic agent than did the other waters.

Thus, the anti-irritant activity of cosmetic compositions containing 2% of 5-n-octanoylsalicylic acid in the eaux du bassin de Vichy was measured in man.

The following results were obtained:

| Thermal spring water | % Inhibition of the irritant effect |
|---|---|
| Eau du bassin de Vichy | 51 |
| Eau de Vittel | 24 |
| Eau du La Roche Posay | 46 |

This application is based on French Patent Application 94-09119, filed on July 22, 1994, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters: Patent of the united states is:

1. A method of reducing the irritant effect caused by a cosmetic and/or dermatological composition comprising an active agent having an irritant side effect when applied to skin, said method comprising incorporating a water having a mineral content of at least 400 mg/l, and a total concentration of carbonate and bicarbonate ions of at least 150 mg/l, in said cosmetic and/or dermatological composition comprising at least one active agent having an irritant side effect, wherein said irritant side effect is responsive to said water.

2. The method of claim 1, wherein said water is a thermal spring water and/or mineral water.

3. The method of claim 1, wherein said thermal spring water and/or mineral water has a mineralization of greater than 700 mg/l.

4. The method of claim 1, wherein said thermal spring water has a concentration of silicon oxide of at least 6 mg/l.

5. The method of claim 1, wherein said active agent having an irritant side effect is a keratolytic agent.

6. The method of claim 1, wherein said keratolytic agent is selected from the group consisting of salicylic acid and derivatives thereof, α-hydroxy acids and derivatives thereof, retinoids and derivatives thereof, benzoyl peroxide, and salts thereof.

7. The method of claim 1, wherein said active agent is a salicylic acid derivative.

8. The method of claim 1, wherein said active agent is selected from the group consisting of 5-n-octanoylsalicylic acid, 5-n-dodecanoylsalicylic acid, 5-n-decanoylsalicylic acid, and quaternary ammonium salts thereof.

9. A cosmetic and/or dermatological composition, comprising at least one active agent having an irritant side effect, in a cosmetically and/or dermatologically acceptable medium, and at least one calming agent selected from thermal spring water and/or mineral water having, a mineral content of at least 700 mg/l, and a total concentration of carbonate and bicarbonate ions of at least 150 mg/l, wherein said irritant side effect is responsive to said water.

10. The composition of claim 9, wherein said water has a total concentration of sodium carbonate and bicarbonate of greater than 2 mg/l.

11. The composition of claim 9, wherein said active agent having an irritant side effect is a keratolytic agent.

12. The composition of claim 9, wherein said keratolytic agent is selected from the group consisting of salicylic acid and derivatives thereof, α-hydroxy acids and derivatives thereof, retinoids and derivatives thereof, benzoyl peroxide, and salts thereof.

13. The composition of claim 9, wherein said keratolytic agent is selected from the group consisting of 5-n-octanoylsalicylic acid, 5-n-dodecanoylsalicylic acid, 5-n-decanoylsalicylic acid, and quaternary ammonium salts thereof.

14. The composition of claim 9, having a concentration of active agent ranging from 0.1% to 5% by weight based on the total weight of said composition.

15. The composition of claim 9, having a concentration of active agent ranging from 0.1% to 2% by weight based on the total weight of said composition.

16. The composition of claim 9, having a concentration of thermal spring water of at least greater than 5% by weight based on the total weight of said composition.

17. The composition of claim 9, which is in the form of a solution, an aqueous gel, an emulsion, or a dispersion of lipid vesicles.

18. The composition of claim 9, further comprising a lipophilic or hydrophilic active agent other than said active agent having an irritant side effect.

19. method of treating acne, wrinkles and/or fine lines on the skin, comprising applying, to the skin, a cosmetic and/or dermatological composition, said cosmetic and/or dermatological composition comprising at least one active agent having an irritant side effect, in a cosmetically and/or dermatologically acceptable medium, and at least one calming agent selected from thermal spring water and/or mineral water having a mineral content of at least 700 mg/l, and a total concentration of carbonate and bicarbonate ions of at least 150 mg/l, wherein said irritant side effect is responsive to said water.

* * * * *